(12) United States Patent
Hirokawa et al.

(10) Patent No.: US 8,744,039 B2
(45) Date of Patent: Jun. 3, 2014

(54) X-RAY CT APPARATUS

(75) Inventors: Koichi Hirokawa, Tokyo (JP); Yoshiaki Sugaya, Tokyo (JP); Taiga Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 728 days.

(21) Appl. No.: 12/999,186

(22) PCT Filed: Jun. 29, 2009

(86) PCT No.: PCT/JP2009/061824
§ 371 (c)(1),
(2), (4) Date: Dec. 15, 2010

(87) PCT Pub. No.: WO2010/001845
PCT Pub. Date: Jan. 7, 2010

(65) Prior Publication Data
US 2011/0091008 A1  Apr. 21, 2011

(30) Foreign Application Priority Data
Jul. 4, 2008  (JP) ................................. 2008-175338

(51) Int. Cl.
H05G 1/34 (2006.01)
A61B 6/03 (2006.01)

(52) U.S. Cl.
USPC .................. 378/16; 378/8; 378/95; 378/108; 378/109; 378/110

(58) Field of Classification Search
USPC ........................... 378/16, 108, 109, 110, 8, 95
See application file for complete search history.

(56) References Cited

U.S. PATENT DOCUMENTS

| | | | | |
|---|---|---|---|---|
| 5,379,333 A | * | 1/1995 | Toth | 378/16 |
| 5,400,378 A | * | 3/1995 | Toth | 378/16 |
| 5,450,462 A | * | 9/1995 | Toth et al. | 378/16 |
| 5,822,393 A | * | 10/1998 | Popescu | 378/108 |

(Continued)

FOREIGN PATENT DOCUMENTS

| | | |
|---|---|---|
| JP | 2004-305527 | 11/2004 |
| JP | 2006-116137 | 5/2006 |

(Continued)

OTHER PUBLICATIONS

International Search Report in PCT/JP2009/061824.

(Continued)

*Primary Examiner* — Allen C. Ho
(74) *Attorney, Agent, or Firm* — Cooper & Dunham LLP

(57) ABSTRACT

An X-ray CT apparatus is provided that generates a three-dimensional cross-section model from scanogram projection data of an examinee. An operator inputs a site of interest, an assumed displacement amount of the site and a desired image quality index value. A scan planning unit calculates an X-ray attenuation index from the three-dimensional cross-section model, and corrects the calculated X-ray attenuation index on the basis of the input site of interest, assumed displacement amount and image quality index value. The scan planning unit further determines a tube current modulating pattern (irradiation X-ray dose modulating pattern) on the basis of the corrected X-ray attenuation index. When scanning is executed, an X-ray tube is controlled according to the determined irradiation X-ray dose modulating pattern, and controlled so as to obtain an optimum X-ray dose.

8 Claims, 14 Drawing Sheets

(56) References Cited

U.S. PATENT DOCUMENTS

| | | | |
|---|---|---|---|
| 5,867,555 A * | 2/1999 | Popescu et al. | 378/16 |
| 6,385,280 B1 * | 5/2002 | Bittl et al. | 378/16 |
| 6,490,337 B1 * | 12/2002 | Nagaoka et al. | 378/20 |
| 6,744,846 B2 * | 6/2004 | Popescu et al. | 378/16 |
| 6,754,301 B2 * | 6/2004 | Horiuchi | 378/16 |
| 6,904,127 B2 * | 6/2005 | Toth et al. | 378/110 |
| 6,987,828 B2 * | 1/2006 | Horiuchi | 378/16 |
| 7,082,183 B2 * | 7/2006 | Toth et al. | 378/16 |
| 7,103,139 B2 * | 9/2006 | Nagaoka et al. | 378/16 |
| 7,106,824 B2 * | 9/2006 | Kazama et al. | 378/16 |
| 7,142,630 B2 * | 11/2006 | Suzuki | 378/16 |
| 7,203,270 B2 * | 4/2007 | Okumura et al. | 378/16 |
| 7,215,733 B2 * | 5/2007 | Nabatame | 378/16 |
| 7,277,523 B2 * | 10/2007 | Mattson | 378/15 |
| 7,336,762 B2 * | 2/2008 | Seto et al. | 378/16 |
| 7,587,023 B2 * | 9/2009 | Hur | 378/16 |
| 7,602,880 B2 * | 10/2009 | Hirokawa et al. | 378/8 |
| 7,668,286 B2 * | 2/2010 | Tsuyuki et al. | 378/8 |
| 7,715,522 B2 * | 5/2010 | Goto et al. | 378/16 |
| 7,945,013 B2 * | 5/2011 | Goto et al. | 378/16 |
| 7,949,087 B2 * | 5/2011 | Hagiwara | 378/4 |
| 2004/0202277 A1 | 10/2004 | Okumura et al. | |

FOREIGN PATENT DOCUMENTS

| | | |
|---|---|---|
| JP | 2007-000446 A | 1/2007 |
| JP | 2008-18044 | 1/2008 |
| JP | 2009-066330 A | 4/2009 |
| KR | 10-0382468 B1 | 5/2003 |
| KR | 10-2004-0050217 A | 6/2004 |
| KR | 10-0638205 B1 | 10/2006 |
| KR | 10-0676767 B1 | 2/2007 |
| KR | 10-2007-0087357 A | 8/2007 |

OTHER PUBLICATIONS

Korean Office Action dated Jun. 11, 2010 issued in Application No. 10-2008-0057361.

Korean Office Action dated Sep. 29, 2010 issued in Application No. 10-2008-0099187.

Korean Office Action dated Sep. 30, 2010 issued in Application No. 10-2008-0099191.

Korean Office Action dated Sep. 30, 2010 issued in Application No. 10-2008-0099193.

Korean Office Action dated Dec. 9, 2010 issued in Application No. 10-2009-0014133.

* cited by examiner

F I G. 1
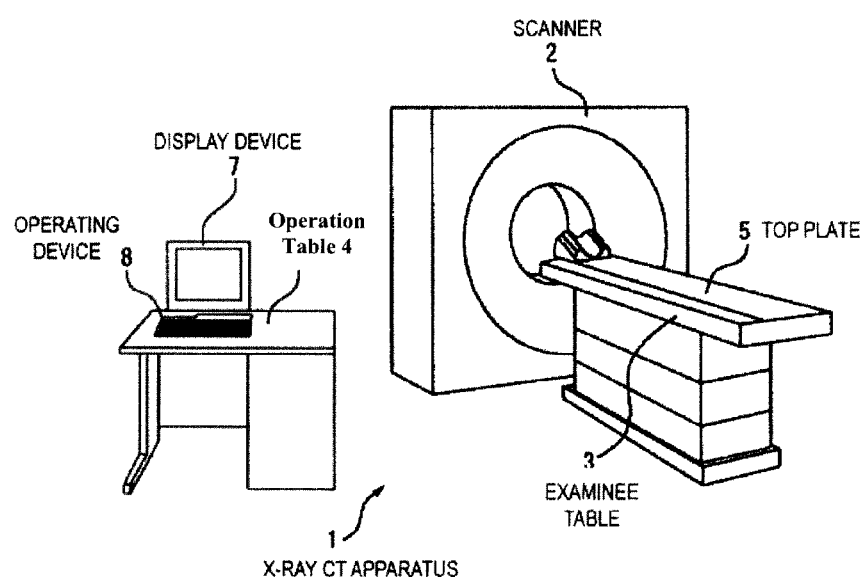

F I G. 3
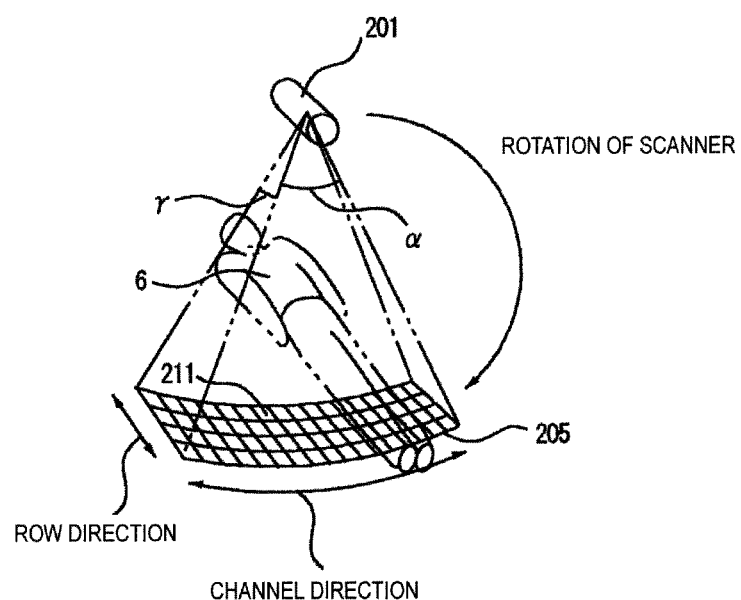

F I G. 4
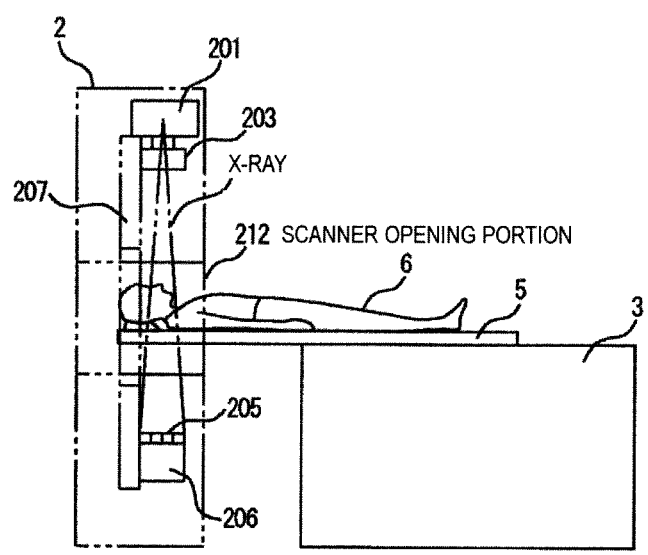

F I G. 7
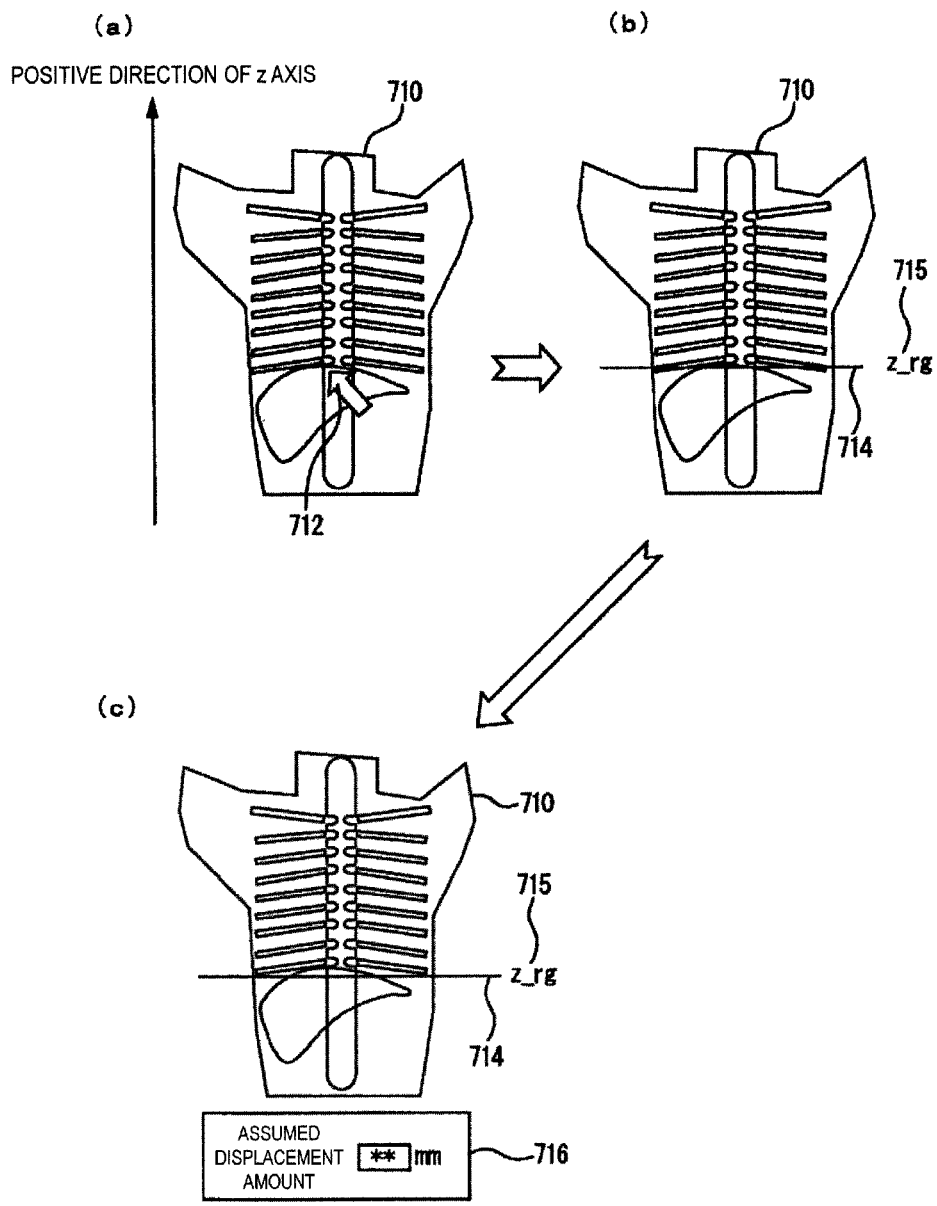

F I G. 8
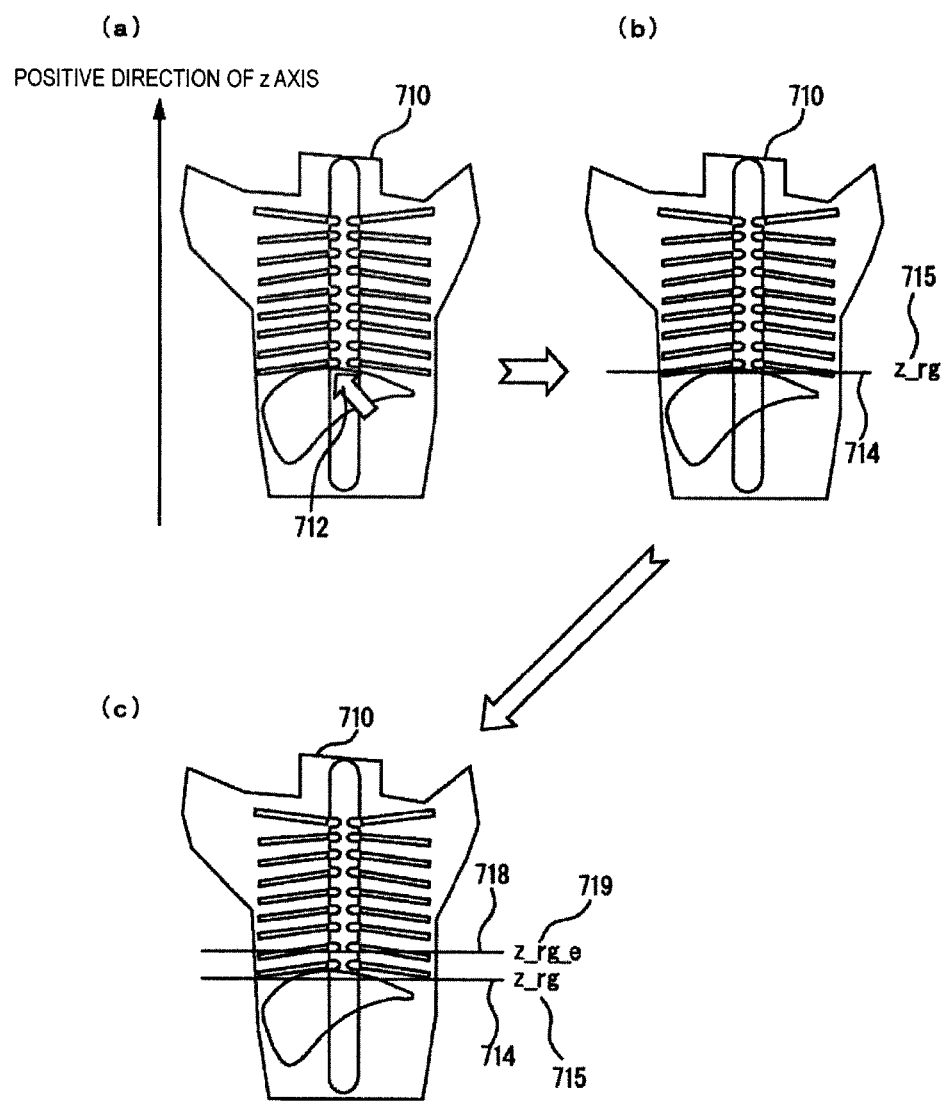

F I G. 9
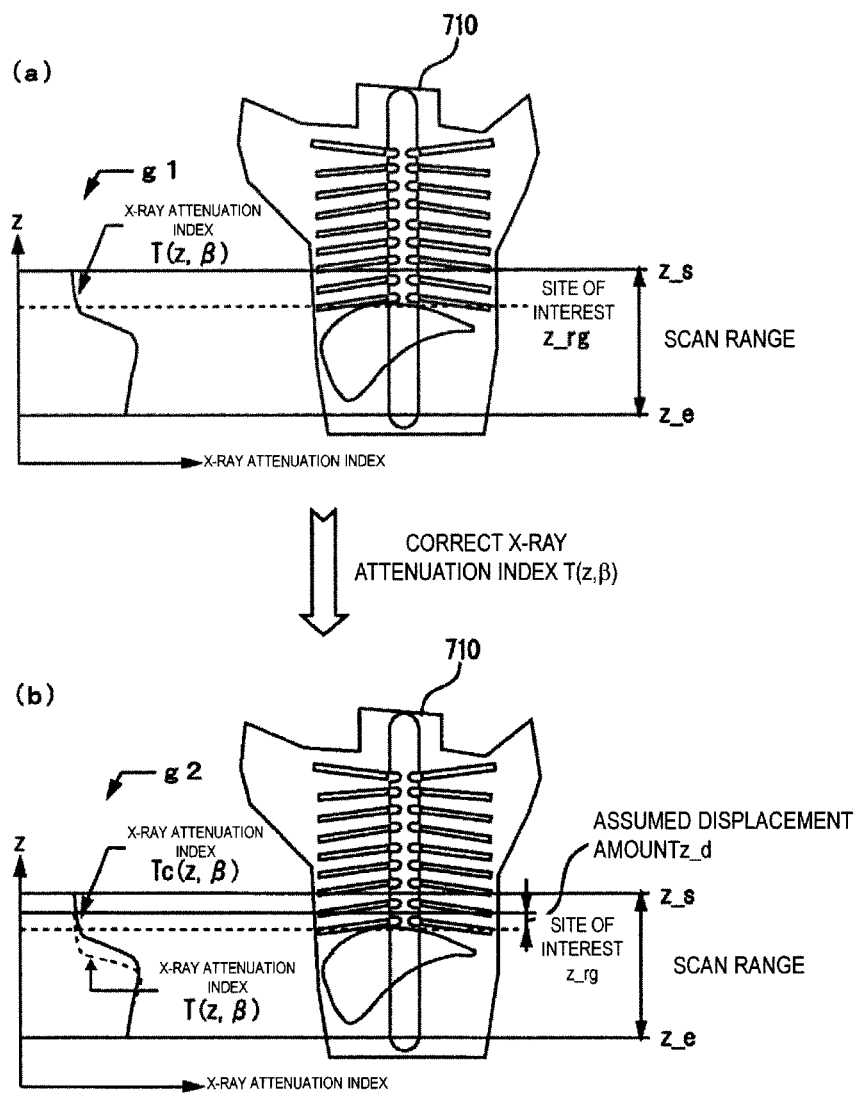

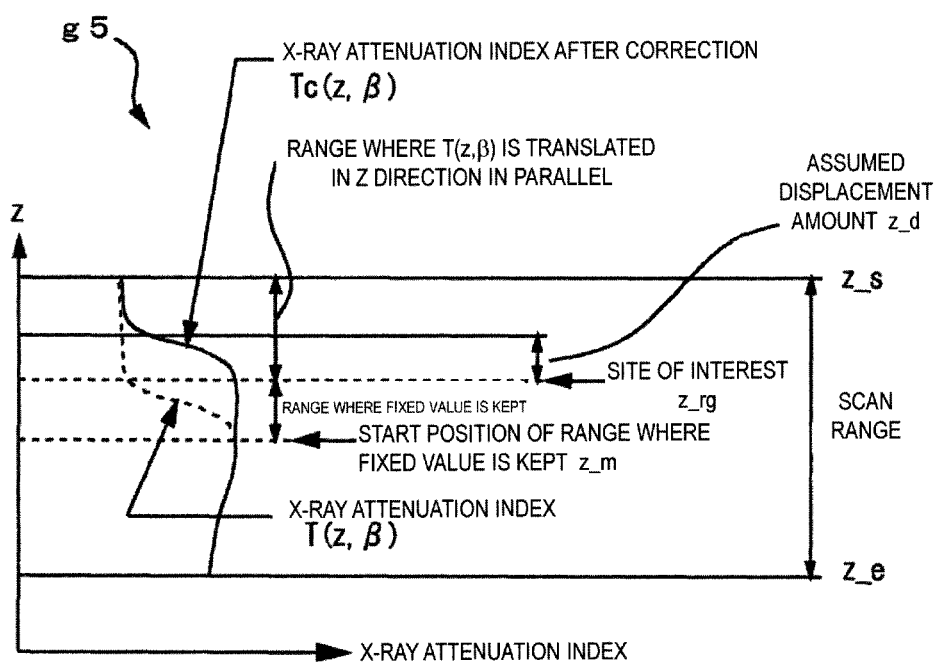
F I G. 1 1

F I G. 1 2
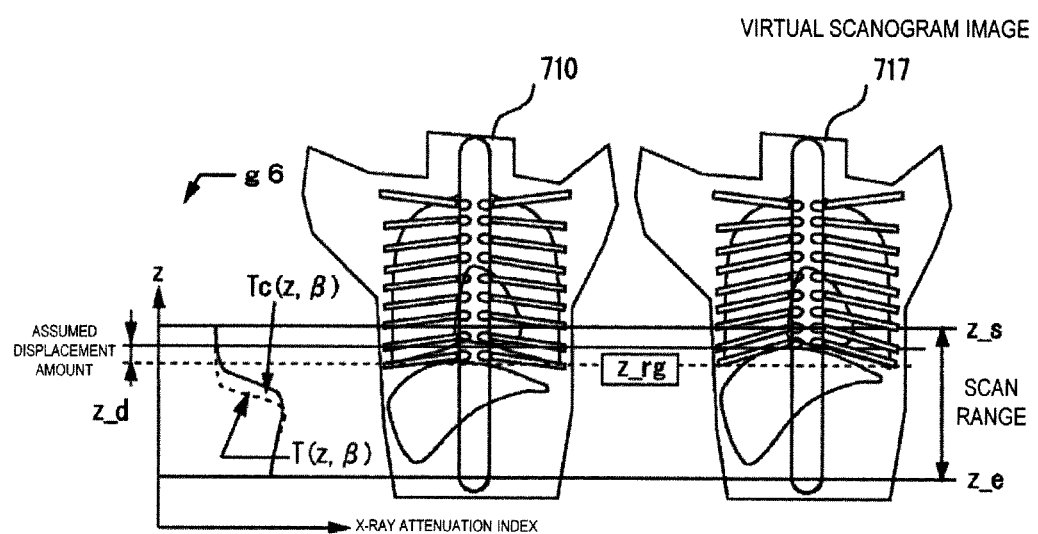

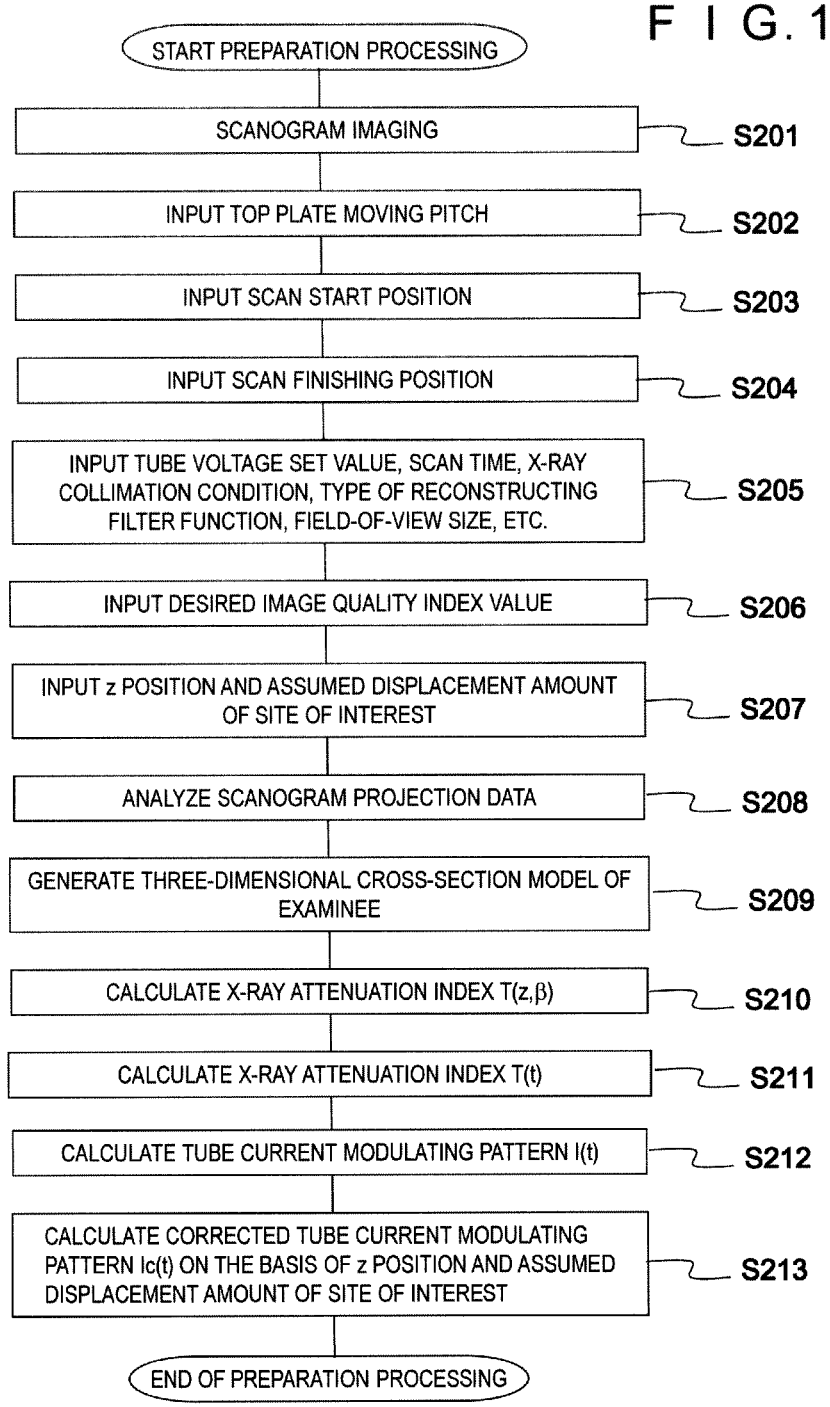

X-RAY CT APPARATUS

TECHNICAL FIELD

The present invention relates to an X-ray CT apparatus, and particularly to an X-ray CT apparatus for controlling the dose of irradiated X-rays under scan in consideration of image quality and the exposed dose.

BACKGROUND ART

The X-ray CT apparatus is a device for irradiates an examinee with a fan-beam (sectorial beam) or cone beam (conical or pyramidal beam) type X-ray to obtain projection data as information concerning the intensity of the X-ray transmitted through the examinee, and images distribution information of an X-ray absorption coefficient of the inside of the examinee on the basis of the projection data.

The X-ray CT apparatus obtains projection data at a discrete X-ray tube position (view). The number of views per rotation of an X-ray tube normally ranges from several hundreds to several thousands. The X-ray CT apparatus irradiates the examinee with X-ray while rotating the X-ray tube around the examinee, thereby performing scanning and obtaining projection data of views whose number is required to reconstruct one tomogram (CT image).

When X-ray tube current is constant as a scan condition of the X-ray CT apparatus, overabundance or deficiency of the exposed dose may occur in accordance with an X-ray irradiation angle or irradiation site. In connection with this, an X-ray CT apparatus for controlling X-ray tube current on the basis of scanogram projection data to lessen the exposed dose and enhance the image quality has been proposed (for example, see "Patent Document 1").

Furthermore, an X-ray CT apparatus for calculating an elliptical cross-sectional model of an examinee from the scanogram projection data and calculating an X-ray tube current value from the area and horizontal to vertical ratio of the elliptical cross-section has been proposed (for example, see Patent Document 2").

PRIOR ART DOCUMENT

Patent Document

Patent Document 1: JP-A-7-124152
Patent Document 2: JP-A-2001-043993

SUMMARY OF THE INVENTION

Problem to be Solved by the Invention

However, a technique of optimizing X-ray tube current disclosed in Patent Document 1 or Patent Document 2 (hereinafter referred to as irradiation X-ray dose) does not assume a case where an internal organ as a scan target is displaced due to breathing or the like of an examinee. Therefore, when the internal organ as the scan target is displaced, a pre-assumed irradiation X-ray dose is not coincident with an irradiation X-ray dose to be actually applied.

On the other hand, when the image quality of a CT image is required to be enhanced, it is necessary to irradiate an examinee with X-ray having a remarkably large irradiation X-ray dose. Therefore, the balance between the irradiation X-ray dose and the image quality has been an important problem in control of the irradiation X-ray dose to lessen the exposed dose.

The present invention has been implemented from the viewpoint of the foregoing problem, and has an object to provide an X-ray CT apparatus that can control an irradiation X-ray dose in accordance with a displacement of an internal organ due to breathing or the like of an examinee with performing both of enhancement of image quality and lessening of the exposed dose.

Means of Solving the Problem

In order to attain the above object, according to the present invention, an X-ray CT apparatus for applying X-ray around an examinee, detecting the dose of X-ray transmitted through the examinee, reconstructing a tomogram of the examinee on the basis of the detected X-ray dose and outputting the tomogram comprises: cross-section model generating means that generates a cross-section model of the examinee by using scanogram projection data of the examinee; input means that inputs a desired image quality index value, a position of a site of interest, an estimated displacement amount in a body axial direction of the site of interest; scan planning means that sets an irradiation X-ray dose modulating pattern corresponding to the image quality index value, the position of the site of interest and the estimated displacement amount input by the input means with respect to the cross-section model generated by the cross-section model generating means; and X-ray control means that modulates an irradiated X-ray dose on the basis of the irradiation X-ray dose modulating pattern set by the scan planning means.

Furthermore, the X-ray CT apparatus further comprises display means that displays a scanogram image generated by using the scanogram projection data, wherein the input means makes an operator instruct an input of any position on the scanogram image displayed by the display means as the position of the site of interest or the estimated displaced position of the site of interest, and the display means demonstrates on the scanogram image the position of the site of interest or the estimated displaced position of the site of interest which is input by the input means.

Furthermore, the scan planning means corrects a scan range in accordance with the estimated displacement amount input by the input means, and sets the irradiation X-ray dose modulating pattern corresponding to the image quality index value, the position of the site of interest and the estimated displacement amount input by the input means in the corrected scan range with respect to the cross-section model generated by the cross-section model generating means.

Furthermore, the scan planning means first calculates an X-ray attenuation index considering the estimated displacement amount as the irradiation X-ray amount modulating pattern corresponding to the image quality index value, the position of the site of interest and the estimated displacement amount input by the input means, and sets the irradiation X-ray dose modulating pattern on the basis of the calculated X-ray attenuation index.

Furthermore, the scan planning means calculates an X-ray attenuation index before estimation of the displacement amount as the irradiation X-ray dose modulating pattern corresponding to the image quality index value, the position of the site of interest and the estimated displacement amount input by the input means in advance, and calculates and sets the irradiation X-ray dose modulating pattern considering the estimated displacement amount on the basis of the calculated X-ray attenuation index.

Furthermore, the X-ray CT apparatus further comprises display means that displays a scanogram image generated by using the scanogram projection data, wherein the scan range corrected by the scan planning means is demonstrated on the scanogram image.

The X-ray CT apparatus further comprises display means that displays a scanogram image generated by using the scanogram projection data, wherein the display means displays a graph corresponding to the X-ray attenuation index while aligning the graph with the scanogram image at a stage that the X-ray attenuation index considering the estimated displacement amount is calculated by the scan planning means.

The X-ray CT apparatus further comprises display means that displays a scanogram image generated by using the scanogram projection data, wherein at each of stages that the X-ray attenuation index before the displacement amount is estimated and the irradiation X-ray dose modulating pattern considering the estimated displacement amount are calculated by the scan planning means, the display means displays each corresponding graph while aligning the graph with the scanogram image.

Effect of the Invention

According to the present invention, there can be provided an X-ray CT apparatus that can control an irradiation X-ray dose in accordance with a displacement of an internal organ caused by breathing or the like of an examinee with performing both of enhancement of image quality and lessening of the exposed dose.

BRIEF DESCRIPTION OF THE DRAWINGS

FIG. 1 is a diagram showing the outlook of an overall construction of an X-ray CT apparatus 1.

FIG. 3 is a diagram showing an X-ray detector 205 and X-ray irradiation.

FIG. 4 is a diagram showing a scanner 2 and scan.

FIG. 7 shows an example of a display screen when a site of interest is specified and an assumed displacement amount is input.

FIG. 8 shows an example of a display screen when the site of interest is specified and the assumed displacement amount is input.

FIG. 9 is a diagram showing correction of an X-ray attenuation index.

FIG. 11 is a diagram showing correction of the X-ray attenuation index.

FIG. 12 shows a display example of a virtual scanogram image 717 in which displacement of an internal organ is assumed.

FIG. 13 is a flowchart showing the flow of the preparation processing when an irradiation X-ray dose modulating pattern is directly corrected.

BEST MODES FOR CARRYING OUT THE INVENTION

Preferred embodiments according to the present invention will be described in detail with reference to the accompanying drawings.

First, the construction of an X-ray CT apparatus 1 according to an embodiment will be described.

Figure 2:
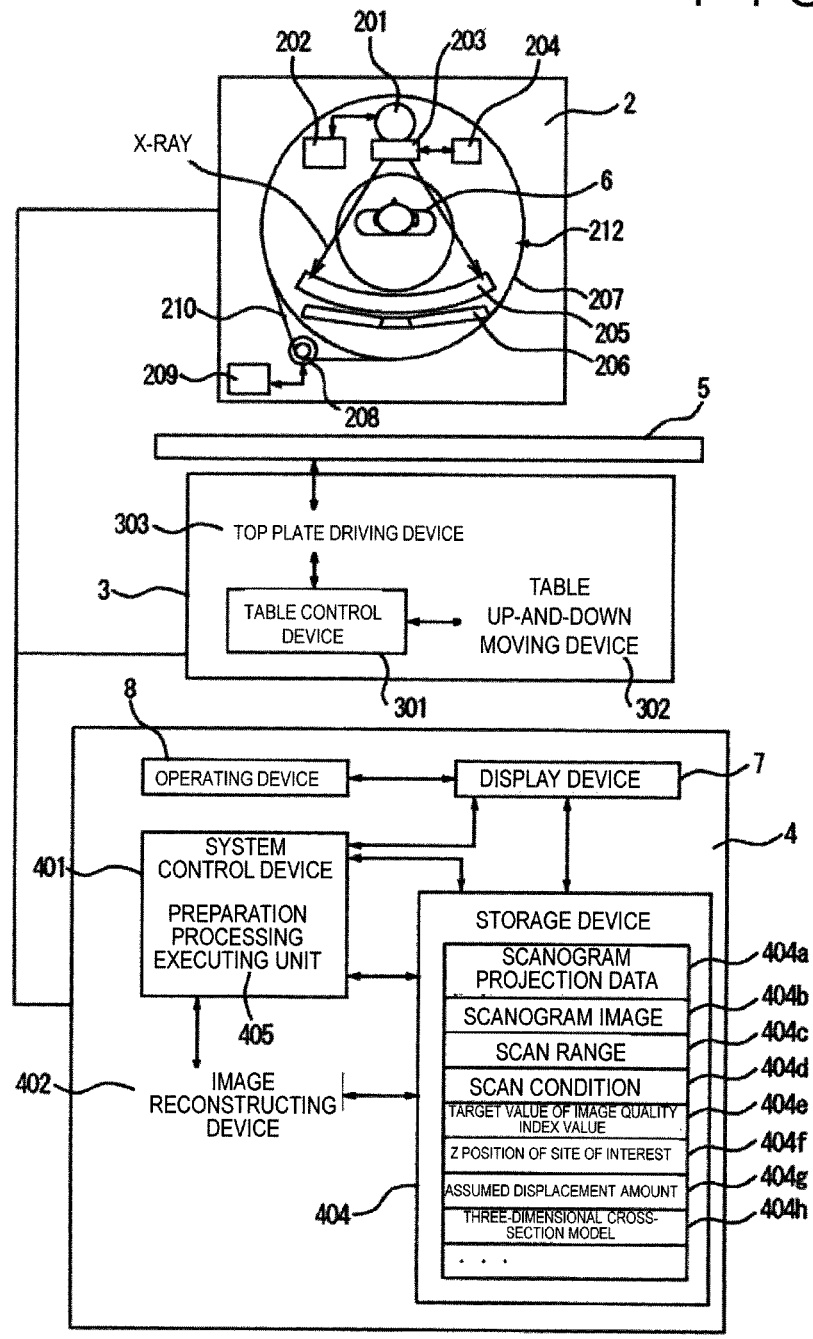
FIG. 2 is a block diagram showing the X-ray CT apparatus 1.

FIG. 1 is a diagram showing the outlook showing the overall construction of the X-ray CT apparatus 1, and FIG. 2 is a block diagram showing the X-ray CT apparatus 1.

In this embodiment, there will be described a case where one X-ray tube is provided, however, the present invention is also applicable to a multiple radiation type X-ray CT apparatus. Furthermore, the X-ray CT apparatus may be based on a Rotate-Rotate type (Rotate-Rotate type) in which an X-ray tube and an X-ray detector are rotated integrally with each other while a wide fan beam covering the whole of an examinee is applied, a Scanning Electron Beam type (Scanning Electron beam type) in which an electron beam is made to impinge against a target electrode while electrically deflected or other types. The present invention is applicable to any type of X-ray CT apparatus.

As shown in FIG. 1, the X-ray CT apparatus 1 comprises a scanner 2, an examinee table 3, an operation table 4, a top plate 5 provided to the examinee table 3, a display device 7 and an operating device 8. The X-ray CT apparatus 1 feeds an examinee 6 fixed to the top plate 5 on the examinee table 3 to an opening portion of the scanner 2 and scans the examinee 6 to obtain X-ray absorption coefficient distribution information of the inside of the examinee 6.

As shown in FIG. 2, scanner 2 comprises an X-ray tube 201, an X-ray tube control device 202, an collimator 203, a collimator control device 204, an X-ray detector 205, a data collecting device 206, a rotating plate 207, a rotating plate driving device 208, a rotation control device 209 and a driving transmission system 210.

The X-ray tube 201 is an X-ray source, and it continuously or intermittently irradiates the examinee 6 with X-ray under the control of the X-ray tube control device 202. The X-ray tube control device 202 controls an X-ray tube voltage and X-ray tube current to be applied and supplied to the X-ray tube 201.

The collimator 203 irradiates the examinee 6 with the X-ray emitted from the X-ray tube 201, for example, as X-ray of cone beam (conical or pyramidal beam) or the like, and is controlled by the collimator control device 204. The X-ray transmitted through the examinee 6 is incident to the X-ray detector 205.

The X-ray detector 205 is disposed so as to face the X-ray tube 201 through the examinee 6. The X-ray detector 205 detects the X-ray which is emitted from the X-ray tube 201 and transmitted through the examinee 6, and outputs detected transmitted X-ray data to the data collecting device 206. The construction of the X-ray detector 205 will be described later.

The data collecting device 206 is connected to the X-ray detector 205, and also collects the transmitted X-ray data detected by each X-ray detecting element 211 (see FIG. 3, described later) of the X-ray detector 205.

On the rotating plate 207 are mounted the X-ray tube 201, the collimator 203, the X-ray detector 205 and the data collecting device 206. The rotating plate 207 is rotated by driving force which is transmitted through the driving transmission system 210 from the rotating plate driving device 208 controlled by the rotation control device 209.

Next, the summary of X-ray irradiation and scan of the X-ray CT apparatus 1 will be described with reference to FIGS. 3 and 4.

FIG. 3 is a diagram showing the X-ray detector 205 and the X-ray irradiation, and FIG. 4 is a diagram showing the scanner 2 and the scan.

As shown in FIG. 3, the X-ray detector 205 is configured by two-dimensionally disposing plural X-ray detecting elements 211 in a channel direction and a column direction. Specifically, the X-ray detecting element 211 is constructed by a combination of a scintillator and a photodiode. For example, about 1 to 1000 X-ray detecting elements 211 are disposed in the channel direction, and about 1 to 1000 X-ray detecting elements 211 are disposed in the column direction. These plural X-ray detecting elements 211 form an X-ray incident face which is curved in a cylindrical surface shape or curved in a polygonal-line shape in the channel direction as a whole. Each X-ray detecting element 211 detects the dose of X-ray transmitted through the examinee 6, and outputs detected transmitted X-ray data to the data collecting device 206. In FIG. 3, an angle represented by $[\alpha]$ is called as a fan angle. The fan angle $[\alpha]$ represents a spreading angle in the channel direction of cone beam X-ray. Furthermore, an angle represented by $[\gamma]$ is called as a cone angle. The cone angle $[\gamma]$ represents a spreading angle in the column direction of the cone beam X-ray.

When the examinee 6 is scanned by the X-ray CT apparatus 1, an opening width of the collimator 203 is adjusted to a desired cone angle $[\gamma]$ and the examinee 6 is exposed with the cone beam X-ray under the state that the examinee 6 put on the top plate 5 of the examinee table 3 is fed in a scanner opening portion 212 as shown in FIG. 4.

The examinee table 3 shown in FIG. 2 comprises the top plate 5, a table control device 301, a table up-and-down moving device 302 and a top plate driving device 303.

The table control device 301 controls the table up-and-down moving device 302 to set a height of the examinee table 3 to a proper height, and also controls the top plate driving device 303 to move the top plate 5 forwardly and backwardly, whereby the examinee 6 is fed into and fed out of an X-ray irradiation space of the scanner 2.

The operation table 4 comprises the display device 7, the operating device 8, a system control device 401, an image reconstructing device 402 and a storage device 404. The operation table 4 is connected to the scanner 2 and the examinee table 3.

The display device 7 comprises a display device such as a liquid crystal panel, and a CRT monitor, and a logical circuit for executing display processing in cooperation with the display device, and is connected to the system control device 401. The display device 7 displays a reconstructed image and a scanogram image output from the image reconstructing device 402 and various information treated by the system control device 401.

The operating device 8 comprises an input device such as a keyboard, a mouse, and ten keys, and various kinds of switch buttons, etc., and outputs various kinds of instructions and information input by an operator to the system control device 401. The operator interactively operates the X-ray CT apparatus 1 by using the display device 7 and the operating device 8. For example, the operating device 8 accepts an input operation of a desired value of an image quality index value described later, a position of a site which is estimated to be easily displaced in a body axis direction due to breathing of the examinee 6 or the like (hereinafter referred to as "site of interest") and an assumed displacement amount of the site of interest on the basis of a scanogram image obtained by the image reconstructing device 402. Furthermore, it accepts an input operation of various kinds of set values such as a scan range and a scan condition.

The system control device 401 comprises CPU (Central Processing Unit), ROM (Read Only Memory), RAM (Random Access Memory) or the like, and it controls the X-ray tube control device 202, the collimator control device 204, the data collecting device 206 and the X-ray detector 205 in the scanner 2 and also controls the table control device 301 in the examinee table 3.

Furthermore, the system control device 401 has a preparation processing executing unit 405 for executing preparation processing executed before the scan operation of the X-ray CT apparatus 1 is started. The preparation processing executing unit 405 will be described later.

The image reconstruction device 402 obtains X-ray projection data collected by the data collecting device 206 in the scanner 2 under the control of the system control device 401. In a scanogram imaging operation, an scanogram image is created by using scanogram projection data collected by the data collecting device 206. Furthermore, in a scanning operation, a tomogram is reconstructed by using X-ray projection data of plural views collected by the data collecting device 206.

The storage device 404 comprises a hard disk or the like, and is connected to the system control device 401. In the storage device 404 are stored scanogram projection data 404a collected by the data collecting device 206 and a scanogram image 404b generated from the scanogram projection data 404a, and also stored a scan range 404c, a scan condition 404d, a target value 404e of a desired image quality index value, a z position 404f of the site of interest and an assumed displacement amount 404g which are input from the operating device 8, a three-dimensional cross-section model 404h generated in the preparation processing before scanning is started, etc. In addition to these various kinds of data, a tomogram generated by the image reconstructing device 402, a program for implementing the function of the X-ray CT apparatus 1, etc. are stored in the storage device 404.

The preparation processing executing unit 405 creates a preliminary plan of scan on the basis of an instruction input from the operating device 8 by an operator's operation, the scanogram projection data 404a read out from the storage device 404, etc. In the following description, a series of processing for creating the preliminary plan of scan is called as preparation processing. The preliminary processing is executed on the basis of a preparation processing program stored in the storage device 404.

Figure 5:
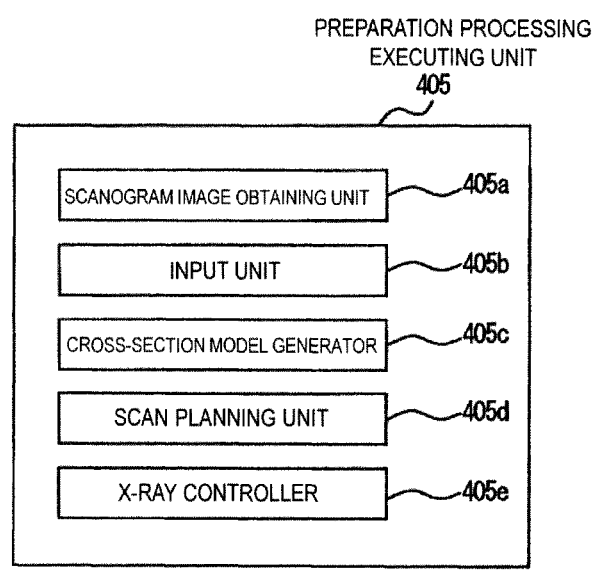
FIG. 5 is a functional block diagram showing a preparation processing executing unit 405.

FIG. 5 is a functional block diagram showing the function of the preparation processing executing unit 405. As shown in FIG. 5, the preparation processing executing unit 405 comprises a scanogram image obtaining unit 405a, an input unit 405b, a cross-sectional model generator 405c, a scan planning unit 405d and an X-ray controller 405e. In addition to the system control device 401 shown in FIG. 2, the operating device 8, the display device 7, the X-ray tube control device 202, the X-ray detector 205, etc. are provided as main constituent elements engaging in the preparation processing.

The scanogram image obtaining unit 405a performs scanogram imaging to obtain a scanogram image of the examinee 6. Furthermore, it executes processing of reading out scanogram projection data 404a which have been obtained by imaging and recorded in the storage device 404. The obtained scanogram projection data 404a or scanogram image 404b is used when a slice position (scan range) of the examinee 6 and a scan condition described later are input.

Here, the scanogram image 404b corresponds to an image obtained by viewing, from one direction, an X-ray image transmitted from the back side to the front side, for example. When a scanogram image is picked up, the X-ray CT apparatus 1 is set so that the examinee table 3 and the rotating plate 207 are relatively moved along the body axis of the examinee 6 without rotating the X-ray tube 201, and irradiates the examinee 6 with X-ray from one direction (for example, from the back side to the front side) to obtain scanogram projection data by the X-ray detector 205. The X-ray CT apparatus 1 transmits the obtained scanogram projection data 404a to the image reconstructing device 402 through the system control device 401. The image reconstructing device 402 creates a scanogram image 404b on the basis of the scanogram projection data 404a, stores it into the storage device 404 and also displays it on the display device 7.

The storage device 404 comprises a hard disk or the like, and is connected to the system control device 401. In the storage device 404 are stored scanogram projection data 404a collected by the data collecting device 206 and a scanogram image 404b generated from the scanogram projection data 404a, and also stored a scan range 404c, a scan condition 404d, a target value 404e of a desired image quality index value, a z position 404f of the site of interest and an assumed displacement amount 404g which are input from the operation device 8, a three-dimensional cross-section model 404h generated in the preparation processing before scanning is started, etc. In addition to these various kinds of data, a tomogram generated by the image reconstructing device 402, a program for implementing the function of the X-ray CT apparatus 1, etc. are stored in the storage device 404.

The preparation processing executing unit 405 creates a preliminary plan of scan on the basis of an instruction input from the operation device 8 by an operator's operation, the scanogram projection data 404a read out from the storage device 404, etc. In the following description, a series of processing for creating the preliminary plan of scan is called as preparation processing. The preliminary processing is executed on the basis of a preparation processing program stored in the storage device 404.

FIG. 5 is a functional block diagram showing the function of the preparation processing executing unit 405.

As shown in FIG. 5, the preparation processing executing unit 405 comprises a scanogram image obtaining unit 405a, an input unit 405b, a cross-sectional model generator 405c, a scan planning unit 405d and an X-ray controller 405e. In addition to the system control device 401 shown in FIG. 2, the operation device 8, the display device 7, the X-ray tube control device 202, the X-ray detector 205, etc. are provided as main constituent elements engaging in the preparation processing.

The scanogram image obtaining unit 405a performs scanogram imaging to obtain a scanogram image of the examinee 6. Furthermore, it executes processing of reading out scanogram projection data which have been obtained by imaging and recorded in the storage device 404. The obtained scanogram projection data or scanogram image is used when a slice position (scan range) of the examinee 6 and a scan condition described later are input.

Here, the scanogram image corresponds to an image obtained by viewing, from one direction, an X-ray image transmitted from the backside to the front side, for example. When a scanogram image is picked up, the X-ray CT apparatus 1 is set so that the examinee table 3 and the rotating plate 207 are relatively moved along the body axis of the examinee 6 without rotating the X-ray tube 201, and irradiates the examinee 6 with X-ray from one direction (for example, from the back side to the front side) to obtain scanogram projection data by the X-ray detector 205. The X-ray CT apparatus 1 transmits the obtained scanogram projection data to the image reconstructing device 402 through the system control device 401. The image reconstructing device 402 creates a scanogram image on the basis of the scanogram projection data, stores it into the storage device 404 and also displays it on the display device 7.

The input unit 405b executes processing of accepting an input of the scan condition. The scan condition contains various kinds of set values such as a scan start position, a scan finishing position, a tube voltage set value, a tube current set value, a time per rotation of the scanner (hereinafter referred to as scan time), an X-ray collimation condition, a type of a reconstructing filter function, and a field-of-view size, and also contains a desired value as a target value of an image quality index value, a position in the body axis direction of the site of interest (hereinafter referred to as z position) and an assumed displacement amount of the site of interest (hereinafter referred to as assumed displacement amount).

Specifically, the input unit 405b displays the input screen for the various kinds of set values on the display device 7 to interactively promote the operator input various kinds of set values. Furthermore, when the operator is made to input the site of interest or the assumed displacement amount of the site of interest, a scanogram image 404b obtained by the scanogram image obtaining unit 405a is displayed on the display device 7 to make the operator input an instruction through a cursor operation of the operating device 8 or the like or input a numerical value by displaying a numerical value input frame on the display device 7. An identification line, etc. are displayed at the input position of the site of interest and the position of the site of interest after the assumed displacement (see FIG. 7, FIG. 8: described later).

The cross-section model generating unit 405e generates a three-dimensional cross-section model of the examinee 6 by using the obtained scanogram projection data 404a. Specifically, the cross-section model generator 405c analyzes the scanogram projection data 404a and models an estimated cross-section at any position along the body axis of the examinee 6 as an elliptical cross-section having an X-ray absorption coefficient equivalent to water, for example. This model is a three-dimensional model in which a major axis length and a minor axis length of the elliptical cross-section vary dependently on the position along the body axis of the examinee 6. This three-dimensional model will be hereinafter referred to as three-dimensional cross-section model. The cross-section model generator 405c stores the generated three-dimensional cross-section model 404h into the storage device 404.

The scan planning unit 405d calculates an optimum irradiation X-ray dose modulating pattern on the basis of the three-dimensional cross-sectional model 404h generated by the cross-sectional model generator 405c, the scan condition input through the input unit 405b, etc. The irradiation X-ray dose modulating pattern is a pattern representing a series of time-dependent variation of the dose of X-ray applied to the examinee 6 under scanning operation. In the following description, a tube current modulating pattern is used as the irradiation X-ray dose modulating pattern. The irradiation X-ray dose modulating pattern is proportional to the tube current modulating pattern.

Furthermore, the scan planning unit 405d in the X-ray CT apparatus 1 according to this embodiment corrects the irradiation X-ray dose modulating pattern (tube current modulating pattern) in accordance with the image quality index value, the site of interest and the assumed displacement amount which are input through the input unit 405b. The calculation and correction of the irradiation X-ray dose modulating pattern (tube current modulating pattern) will be described in detail later. Furthermore, the scan planning unit 405d graphs curved lines representing respective irradiation X-ray dose modulating patterns (tube current modulating patterns) in a case where scanning is performed with correcting the irradiation X-ray dose and a case where scanning is performed without correcting the irradiation X-ray dose, and displays these graphs on the display device 7 in alignment with the displayed scanogram image. Furthermore, The scan planning unit 405d may also graph the X-ray attenuation index calculated in the process of calculating the irradiation X-ray dose modulating pattern, and displays the graph on the display device 7 in alignment with the scanogram image.

Next, the X-ray controller 405e controls the X-ray tube control device 202 on the basis of the irradiation X-ray dose modulating pattern calculated by the scan planning unit 405d to optimize the X-ray amount to be applied.

The operation of the X-ray CT apparatus 1 will be described with reference to FIGS. 6 to 12.

Figure 6:
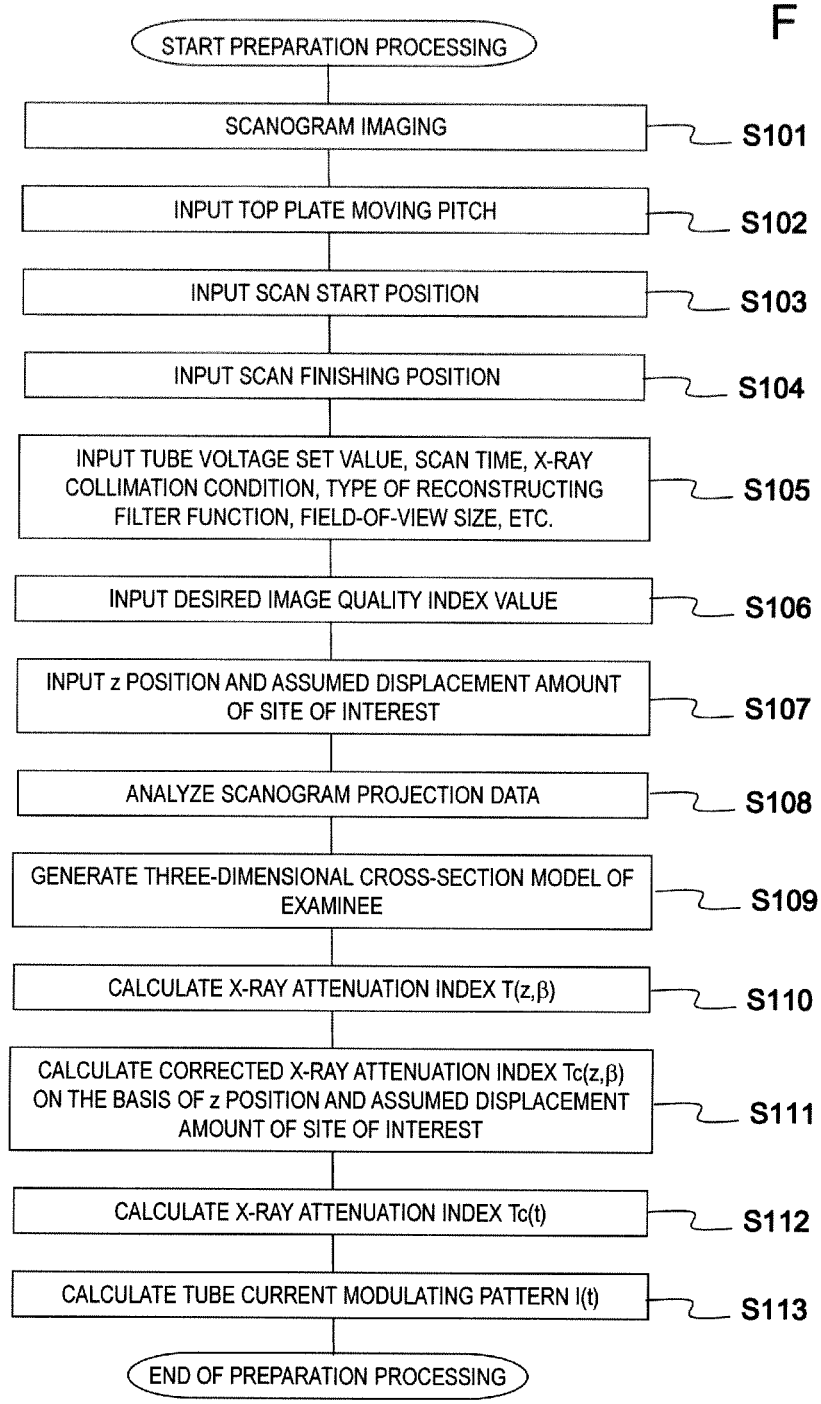
FIG. 6 is a flowchart showing the operation of the preparation processing of the X-ray CT apparatus 1.

FIG. 6 is a flowchart showing the operation of the preparation processing of the X-ray CT apparatus 1, and FIGS. 7 and 8 show display screen examples when the site of interest is specified and the assumed displacement amount is input.

Figure 10:
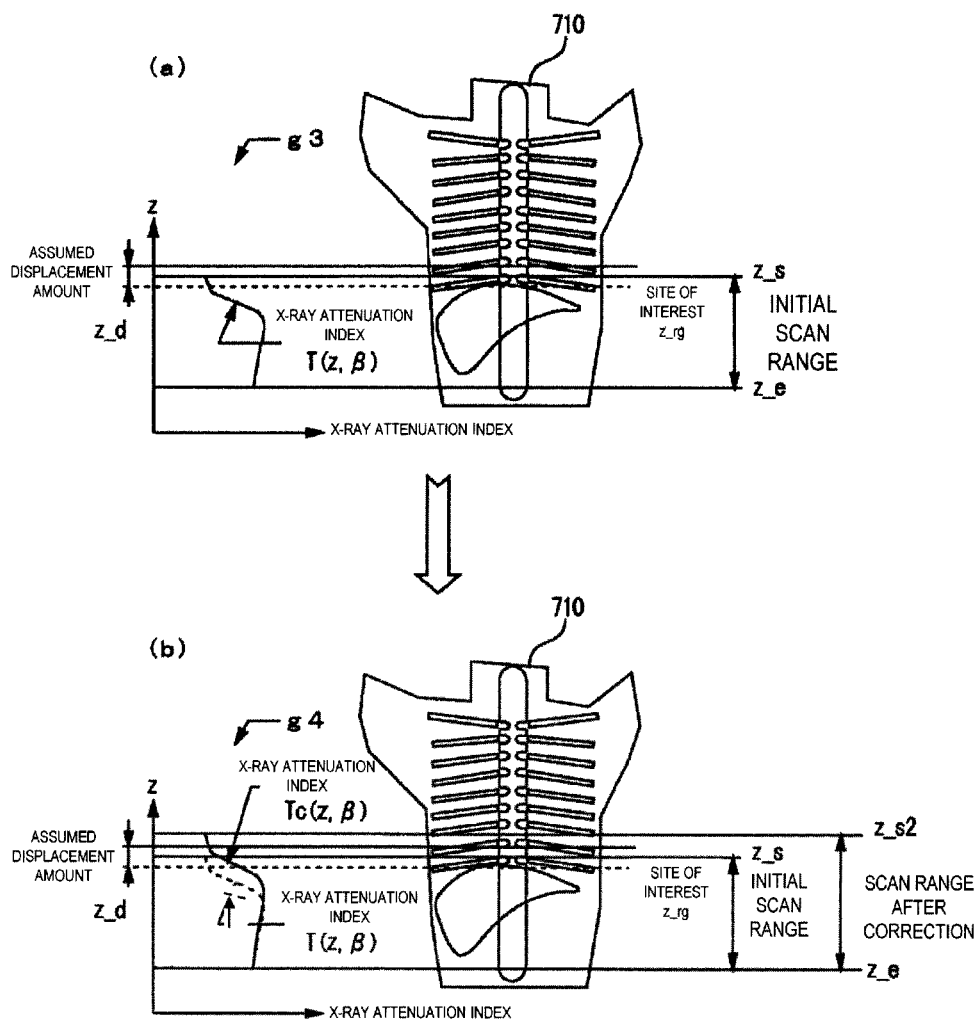
FIG. 10 is a diagram showing correction of the X-ray attenuation index.

FIGS. 9 to 11 are diagrams showing a correction of the X-ray attenuation index, and FIG. 12 shows a display example of a virtual scanogram image for which displacement of an internal organ is assumed.

The preparation processing executed by the X-ray CT apparatus 1 will be described with reference to FIGS. 6 to 12. The preparation processing executing unit 405 of the X-ray CT apparatus 1 according to this embodiment executes the preparation processing before scanning is started. That is, the system control device 401 reads out a program and data concerning execution of the preparation processing from the storage device 404, and executes the preparation processing on the basis of the program and the data.

In the preparation processing, the scanogram image obtaining unit 405a of the preparation processing executing unit 405 performs scanogram imaging of the examinee 6, and obtains scanogram projection data (step S101). The scanogram image obtaining unit 405a transmits the obtained scanogram projection data 404a to the image reconstructing device 402. The image reconstructing device 402 creates a scanogram image 404b on the basis of the scanogram projection data 404a, and it stores the scanogram image 404b into the storage device 404 and displays the scanogram image 404b on the display device 7.

Subsequently, the input unit 405b makes the display device 7 display an input screen for setting a scan range and a scan condition, and promotes the operator to input setting of the scan range and the scan condition. The operator sets the scan range and the scan condition on the basis of a displayed scanogram image 710 by using the operating device 8 (steps S102 to S105). Here, the scan range is displayed at the position in the body axis direction of the examinee 6 at the scanning time, and specifically it is determined by the scan start position (step S103) and the scan finishing position (step S104). The scan start position means the z position of a first tomogram obtained by a series of scan and the scan finishing position means the z position of a last tomogram. A body-axis direction imaging range (z position) and a phase angle [β] (a phase angle of the rotating plate 207) of the X-ray tube 201 are determined.

Furthermore, the scan condition contains a movement pitch of the top plate 5 (step S102), a tube voltage setting value, a scan time, an X-ray collimation condition, a kind of a reconstructing filter function, a field-of-view size, etc. (step S105), for example. The input unit 405b saves the set scan range 404c and scan condition 404d into the storage device 404.

Furthermore, the operator inputs a target value of a desired image quality index value 404e by using the operating device 8 (step S106). For example, an image quality SD (Standard Deviation) value, CNR (contrast noise ratio), an identifiable diameter (radius of identifiable abnormal shade and shadow) under predetermined CNR, SNR (signal nose ratio) or the like is used as the image quality index value. In the following description, it is assumed that the image SD value is used as the image quality index value as an example.

Furthermore, the operator inputs the z position 404f and assumed displacement amount of the site of interest by using the operating device 8 (step S107). The assumed displacement amount is a displacement in the z direction (body axial direction), and it may be in any direction of the positive and negative directions.

Here, a specific example when the z position and assumed displacement amount of the site of interest are input in step S107 will be described with reference to FIGS. 7 and 8. As shown in FIG. 7(a), the X-ray CT apparatus 1 first displays the scanogram image 710 picked up in step S101 and also displays a cursor 712 on the display device 7. The cursor 712 is used to instruct and input any position on the display screen, and it can be moved to any position by using a pointing device such as a mouse of the operating device 8. At the stage of FIG. 7(a), the z position of the site of interest is instructed and input by the cursor 712. When the z position of the site of interest is input, the X-ray CT apparatus 1 displays a site-of-interest line 714 at the input z position on the scanogram image 710 as shown in FIG. 7(b). Furthermore, for example, [z_rg] as a z coordinate of the site-of-interest line 714 is displayed as a site-of-interest symbol 715 in the neighborhood of the site-of-interest line 714.

Subsequently, as shown in FIG. 7(c), the X-ray CT apparatus 1 displays an input frame 716 for inputting the assumed displacement amount on the display device 7. In the example of FIG. 7(c), the input frame 716 is displayed like "assumed displacement amount **mm" to promote input of a numerical value.

FIG. 8 shows another specific example. As in the case of FIG. 8(a) and FIG. 7(a), the scanogram image 710 and the cursor 712 are displayed. When the operator inputs the z position of the site of interest by using the cursor 712, the X-ray CT apparatus 1 displays the site-of-interest line 714 and the site-of-interest symbol 715 as shown in FIG. 8(b). Thereafter, when a position ([z_rg_e] position) after the assumed displacement of the site of interest is instructed and input by using the cursor 712, a line 718 after the assumed displacement is displayed at the position after the assumed displacement, and also [z_rg_e] as the z coordinate of the line 718 after the assumed displacement, for example, is displayed as a symbol 719 after the assumed displacement. Here, an assumed displacement amount [z_d] is represented by the following mathematical expression.

$$z\_d = z\_rg\_e - z\_rg$$

The input unit 405b saves the thus-input image quality index value 404e, z position of the site of interest 404f and assumed displacement amount 404g into the storage device 404.

Subsequently, the cross-section model generator 405c reads out the scanogram projection data 404a from the storage device 404 and executes analysis processing of the scanogram projection data (step S108). Furthermore, the cross-section model generator 405c generates a three-dimensional cross-section model 404h of the examinee 6 on the basis of data of a reference human body model stored in the storage device 404 (step S109).

The scan planning unit 405d creates a scan plan corresponding to the scan range 404c, the scan condition 404d, the desired image quality index value 404e, the z position of the site of interest 404f and the assumed displacement amount 404g stored in the storage device 404.

In the following description concerning the creation of the scan plan, the preparation processing executing unit 405 successively executes calculating operations for obtaining an irradiation X-ray dose modulating pattern adaptive to the assumed displacement amount, and in this example, the tube current modulating pattern is used as an example of the irradiation X-ray dose modulating pattern.

First, the scan planning unit 405d calculates an X-ray attenuation index T at each z position of scan and each phase angle [β] of the X-ray tube 201 (step S110).

The X-ray attenuation index T is an integration value of an X-ray absorption coefficient distribution along an X-ray transmission path. The X-ray transmission path is a path of X-ray passing through the center of the elliptical cross-section of the three-dimensional cross-section model 404h. T(z, β) represents a calculation result of the X-ray attenuation index T with respect to X-ray which is incident to the elliptical cross-section at the z position of the three-dimensional cross-section model 404h from the phase angle [β]. The X-ray attenuation index T is calculated on the basis of the three-dimensional cross-section model 404h generated in step S109. The scan planning unit 405d reads out the three-dimensional cross-section model 404h from the storage device 404 and calculates the X-ray attenuation index T(z, β) with respect to the three-dimensional cross-section model 404h.

Subsequently, the scan planning unit 405d corrects the X-ray attenuation index T(z, β) calculated in step S110 on the basis of the z position [z_rg] and the assumed displacement amount [z_d] of the site of interest. The corrected X-ray attenuation index is represented by Tc(z, β) (step S111). The corrected X-ray attenuation index Tc(z, β) is calculated by using the mathematical expression (1).

[Expression 1]

$$Tc(z, \beta) = \begin{cases} T\left(z\_e + \frac{z\_rg - z\_e}{z\_rg + z\_d - z\_e} * (z - z\_e), \beta\right)(z\_e \leq z \leq z\_rg + z\_d) \\ T\left(z\_s + \frac{z\_rg - z\_s}{z\_rg + z\_d - z\_s} * (z - z\_s), \beta\right)(z\_rg + z\_d < z \leq z\_s) \end{cases} \quad (1)$$

Here, the calculation of the x-ray attenuation index Tc(z, β) will be described with reference to FIG. 9.

In FIG. 9, [z_s] represents the scan start position, and [z_e] represents the scan finishing position. A range from the scan start position [z_s] to the scan finishing position [z_e] is a scan range. In the example of FIG. 9, the positions of the indicated site of interest [z_rg] and the site of interest after the assumed displacement are within the scan range.

A curved line drawn in a graph g1 of FIG. 9(a) represents the X-ray attenuation index T(z, β) calculated in step S110. A z axis of the graph g1 corresponds to the z axis (body axis) of the scanogram image, and also it corresponds to the z position of the graph and the z position on the scanogram image. The same is satisfied in the graphs shown in FIGS. 9 to 12 and FIG. 14.

When the scanogram image 710 and the graph g1 are compared with each other in FIG. 9(a), a curved line representing an X-ray attenuation index increasing in the neighborhood of the site of interest [z_rg] is drawn. In a graph g2 of FIG. 9(b), a curved line indicated by a solid line represents the X-ray attenuation index Tc(z, β) after correction, and a curved line indicated by a dashed line represents the X-ray attenuation index T(z, β) before correction. Tc(z, β) calculated according to the mathematical expression (1) is corrected to draw a curved line representing an X-ray attenuation index increasing at the z position nearer to the site of interest after the assumed displacement as compared with the scanogram image 710.

Furthermore, FIG. 10 shows an example in which the position of the site of interest deviates from the scan range after the assumed displacement. A curved line indicated in a graph g3 of FIG. 10(a) represents the X-ray attenuation index T(z, β) calculated in step S110. As in the case of FIG. 9(a), a curved line representing an X-ray attenuation index increasing in the neighborhood of the site of interest [z_rg] is drawn as compared with the scanogram image 710. On the other hand, as shown in FIG. 10(b), when the position of the site of interest after the assumed displacement from the site of interest [z_rg] is deviated from the initial scan range, a scan start position [z_s] is first corrected by using the mathematical expression (2), and it is represented by [z_s2].

[Mathematical Expression 2]

$$z\_s2 = z\_s + z\_d \quad (2)$$

Thereafter, the X-ray attenuation index T(z, β) calculated in step S110 is corrected by using the mathematical expression (3).

[Mathematical Expression 3]

$$Tc(z, \beta) = \begin{cases} T\left(z\_e + \frac{z\_rg - z\_e}{z\_rg + z\_d - z\_e} * (z - z\_e), \beta\right)(z\_e \leq z \leq z\_rg + z\_d) \\ T\left(z\_s2 + \frac{z\_rg - z\_s2}{z\_rg + z\_d - z\_s2} * (z - z\_s2), \beta\right)(z\_rg + z\_d < z \leq z\_s2) \end{cases} \quad (3)$$

In a graph g4 of FIG. 10(b), a curved line indicated by a solid line represents the X-ray attenuation index Tc(z, β) after correction, and a curved line indicated by a dashed line represents the X-ray attenuation index T(z, β) before correction. As compared with the scanogram image 710, the X-ray attenuation index Tc(z, β) after correction is corrected to draw a curved line along which the X-ray attenuation index increases at a position nearer to the position of the site of interest after the assumed displacement as in the case of FIG. 9.

As in the case of the example shown in FIGS. 9 and 10, the X-ray CT apparatus 1 may make the display device 7 display the scanogram image 710 and the graphs g1, g2 (or the graphs g3, g4) every time the X-ray attenuation index T(z, β) or Tc(z, β) is calculated. In this case, the operator can check the X-ray attenuation index before correction and the X-ray attenuation index after correction which are displayed on the display device 7 while comparing them with the scanogram image 710.

As in the case of the example shown by a graph g5 of FIG. 11, the operator may directly specify a start position [z_m] in a range where the X-ray attenuation index is kept constant in step S110. In the graph g5, a solid line represents the X-ray attenuation index after correction, and a dashed line represents the X-ray attenuation index before correction. In the example of FIG. 11, as shown in the graph g5, the z position at which the X-ray attenuation index T(z, β) calculated in step S110 has a maximum value is specified as the start position [z_m] of the range where the X-ray attenuation index is kept constant (hereinafter referred to as constant range). When the X-ray attenuation index is corrected, the range from the start position [z_m] of the constant range to the site of interest [z_rg] is set so as to keep a value of the X-ray attenuation index to a fixed value. Furthermore, with respect to the X-ray attenuation index Tc(z, β) in the range from the site of interest [z_rg] to the scan start position [z_s], the X-ray attenuation index T(z, β) in the range from [z_m] to [z_s−(z_rg−z_m)] of the X-ray attenuation index before correction is translated in the z direction.

As in the case of the example of FIG. 11, by correcting the X-ray attenuation index so that the range where the X-ray attenuation index is kept to a value in the neighborhood of the maximum value thereof, even when the site of interest (internal organ) is displaced, the X-ray attenuation index in the corrected range is also sufficiently large and thus the irradiation X-ray dose corresponding to the X-ray attenuation index is sufficiently large, so that sufficient image quality can be achieved.

As described above, at the stage that the X-ray attenuation index is corrected, the scan planning unit 405d may make the display device 7 display a virtual scanogram image 717 which assumes a displacement of the internal organ as shown in FIG. 12.

FIG. 12 shows the scanogram image 710 of the examinee 6, the virtual scanogram image 717 and a graph g6. The virtual scanogram image 717 represents a state that the internal organ at the site of interest (in this case, liver) is displaced by only the assumed displacement amount [z_d], and it can be generated by processing an image on the basis of the scanogram image 710 and the assumed displacement amount. A curved line indicated by a dashed line of the graph g6 represents the X-ray attenuation index T(z, β) before correction, and a curved line indicated by a solid line represents the X-ray attenuation index Tc(z, β) after correction.

At the stage that the step S111 is finished and the X-ray attenuation index after correction is calculated, the preparation processing executing unit 405 subjects the scanogram image 710 to processing such as movement of the internal organ as the site of interest, and deformation of the shape of the internal organ on the basis of the assumed displacement amount to generate the virtual scanogram image 717. The preparation processing executing unit 405 displays the generated virtual scanogram image 717 on the display device 7.

As shown in FIG. 12, the scanogram image 710 and the virtual scanogram image 717 are displayed side by side, and the curved line of each of the X-ray attenuation indexes before and after correction is displayed to be identifiable as in the case of the graph g6, whereby the displacement of the site of interest can be visually recognized. Furthermore, the graph of the X-ray attenuation index which is corrected in accordance with the displacement can be checked in comparison with the scanogram images 710, 717. Therefore, the operator clearly grasps on the display screen that the X-ray dose is optimally controlled in accordance with the displacement of the site of interest.

Subsequently, the scan planning unit 405d converts a function of the X-ray attenuation index Tc from Tc=Tc(z, β) to a function Tc=Tc(t) of a time t from the X-ray attenuation index Tc calculated through the above processing on the basis of the input scan start position, scan finishing position, top plate moving pitch and scan time (step S112).

Furthermore, the scan planning unit 405d calculates a tube current modulating pattern I(t) represented by the function of the scan time t (step S113). The calculation of the tube current modulating pattern I(t) will be described hereunder in detail.

First, the scan planning unit 405d calculates a tube current value $i_v(m)$ every view.

In the following description, [M] represents the number of views used to reconstruct a tomogram Img(z) at the z position, [N] represents the number of views per rotation, and [m] represents a convenient view number m (0≤m≤M−1).

The number of views being used [M] is not necessarily equal to the number of views per rotation (N). Tc_max(0:M−1) represents a maximum value of the X-ray attenuation index Tc in the range (0≤m≤M−1) of the view number m.

The tube current value $i_v(m)$ corresponding to the view number [m] can be presented by the mathematical expression (4) on the assumption that a reference tube current value [i_ref] at Tc_max (0:M−1) is made to correspond to the tube current value $i_v(m)$.

[Mathematical Expression 4]

$$i_v(m) = i\_ref * \exp(Tc(m) - Tc\_\max(0:M-1)) \quad (4)$$

An image noise variance V is represented as the function of the X-ray attenuation index Tc like the mathematical expression (5).

[Mathematical Expression 5]

$$V(Tc, i\_ref, trot\_ref, thk\_ref) = c((xv, g, i\_ref, trot\_ref, thk\_ref) * \exp(a(xv) * Tc) \quad (5)$$

Here, it is assumed in the mathematical expression (5) that a time [trot] in which the scanner 2 rotates once is equal to a reference time [trot_ref] and the X-ray attenuation index is equal to a fixed value during this time. Furthermore, it is also assumed that [xv] is used as the tube voltage and the reference tube current [i_ref] is used as a tube current value [i]. Still further, it is also assumed that the number of views per rotation [N-ref] is equally weighted, a reconstructing filter function [g] is used and reconstruction is performed by setting an image thickness [thk] to a reference image thickness [thk_ref].

Here, a (xv) represents a constant dependent on the tube voltage [xv]

b(xv,g) represents a constant dependent on the tube voltage [xv] and the reconstructing filter function [g]

[Mathematical Expression 6]

$$c(xv, g, i, trot, thk) = \frac{b(xv, g) * i\_ref * trot\_ref * thk\_ref}{i * trot * thk} \quad (6)$$

a(xv), b(xv, g) are stored in the storage device 404 in advance.

An image noise dispersion prediction value V* when the tube current value $[i_v(m)]$ represented by the above mathematical expression (4) is represented by the mathematical expression (7).

[Mathematical Expression 7]

$$V^* = N * \sum_{m=0}^{M-1} \left( w(m) \Big/ \sum_{m=0}^{M-1} w(m) \right)^2 * V(Tc(m), i_v(m), trot, thk) \quad (7)$$

Here, w(m) of the mathematical expression (7) represents a view direction weight applied to each view. The view direction weight is used when the number of views [M] used for reconstruction is different from the number of views [N] per rotation or when an artifact based on movement of the examinee 6 is corrected (G. Wang, et al. "Half-Scan Cone-Beam X-ray Microtomography Formula" Journal of Scanning Microscopies Vol. 16, 216-220(1994), JP-A-08-280664).

Furthermore, [trot], [thk] represent the set values of the scan condition 404d to scan to be executed from now, wherein [trot] represents the time required for the scanner 2 to make one rotation, [thk] represents an image thickness.

When the number of views being used [M] is equal to the number of views per rotation [N], so-called full-scan reconstruction can be performed by setting as follows:

[Mathematical Expression 8]

$$w(m)=1 \ (m=0 \text{ to } N-1) \quad (8)$$

Here, a tube current value $i_a$ (m) which should be actually applied is settled from a desired image noise variance [Vtgt] (squire value of SDtgt) determined from a desired value [SDtgt] of the image SD value input by the operator and the image noise variance prediction value V* of the mathematical expression (7) according to the mathematical expression (9).

[Mathematical Expression 9]

$$i_a(m) = i_v(m) * \frac{V^*}{Vtgt} \quad (9)$$

As described above, a series of tube current values (hereinafter referred to as tube current modulating pattern) for implementing the desired value of the image SD value input by the operator in the tomogram at each z position can be determined. When the tube current modulating pattern is represented by I, the tube current modulating pattern I can be represented by a function I(t) of the elapse time [t] after scan is started (step S112).

That is, in step S112, the scan planning unit 405d sets a tube current standard modulation curved line [$i_v$(m)] for varying the X-ray dose applied from the X-ray tube 201 every view on the basis of the three-dimensional cross-section model. Further, the scan planning unit 405d corrects the above tube current standard modulation curved line [$i_v$(m)] on the basis of a ratio between the image noise dispersion prediction value V* when the X-ray dose corresponding to the set tube current standard modulation curved line [$i_v$(m)] is applied and the desired image noise variance Vtgt settled from the desired value [SDtgt] of the image SD value, thereby determining a tube current modulation curved line [$i_a$(m)] representing an optimum irradiation X-ray dose (tube current value) for attaining the desired value [SDtgt] of the image SD value described above. Then, the tube current modulating pattern I(t) is modulated on the basis of the thus-determined tube current modulation curved line [$i_a$(m)].

The scan planning unit 405d saves the determined tube current modulating pattern I=I(t) into the storage device 404.

The X-ray controller 405e successively calls the tube current modulating pattern I in accordance with an imaging site of the examinee 6 when scan is executed, and controls the tube current in the scan through the X-ray tube control device 202.

As described above, the X-ray CT apparatus 1 of this embodiment generates the three-dimensional cross-section model by using the scanogram projection data of the examinee 6 before actual scan, inputs the desired image quality index value, the z position of the site of interest and the assumed displacement amount of the site of interest, and sets the irradiation X-ray dose modulating pattern (tube current modulating pattern) which is proper to the three-dimensional cross-section model, the input image quality index value, site of interest and assumed displacement amount. The X-ray CT apparatus 1 controls the X-ray dose to be applied to the examinee 6 on the basis of the set irradiation X-ray dose modulating pattern (tube current modulating pattern). Therefore, even when the site of interest is displaced due to breathing or the like, proper image quality can be secured. Accordingly, the irradiation X-ray dose can be controlled in accordance with the displacement of the internal organ caused by breathing of the examinee 6 or the like with satisfying both the enhancement of the image quality and the lessening of exposed dose.

Furthermore, in accordance with the input estimated displacement amount, at least one of the start position and the finishing position of the scan range is corrected, and the proper irradiation X-ray dose modulating pattern is set in the corrected scan range. Accordingly, even when the site of interest is deviated from the initially set scan range due to the displacement caused by breathing or the like, the scan range is automatically corrected and the optimum irradiation X-ray dose modulating pattern is calculated, whereby scan can be performed with the optimum X-ray dose.

Furthermore, the X-ray CT apparatus 1 makes the display device 7 display the scanogram image 710 of the examinee 6, and the operator can instruct and input any position on the scanogram image 710 as the position of the site of interest or the position after the estimated displacement of the site of interest by the cursor 712 or the like, so that the input operation can be easily performed. Furthermore, the position of the site of interest or the position after the assumed displacement of the site of interest is demonstrated on the scanogram image 710 at each stage, so that interactive operation can be performed.

The X-ray CT apparatus 1 graphs the calculated irradiation X-ray dose modulating pattern to display the graphed irradiation X-ray dose modulating pattern in alignment with the scanogram image 710, and generates and displays the virtual scanogram image 717 obtained by moving the input site of interest or deforming the shape of the input site of interest in accordance with the assumed displacement amount, so that the operator can easily and clearly check the optimum irradiation X-ray dose modulating pattern corresponding to the displacement.

In the above example, the irradiation X-ray dose modulating pattern after the assumed displacement is determined by correcting the X-ray attenuation coefficient first. However, the irradiation X-ray dose modulating pattern (tube current modulating pattern) may be directly corrected.

Figure 14:
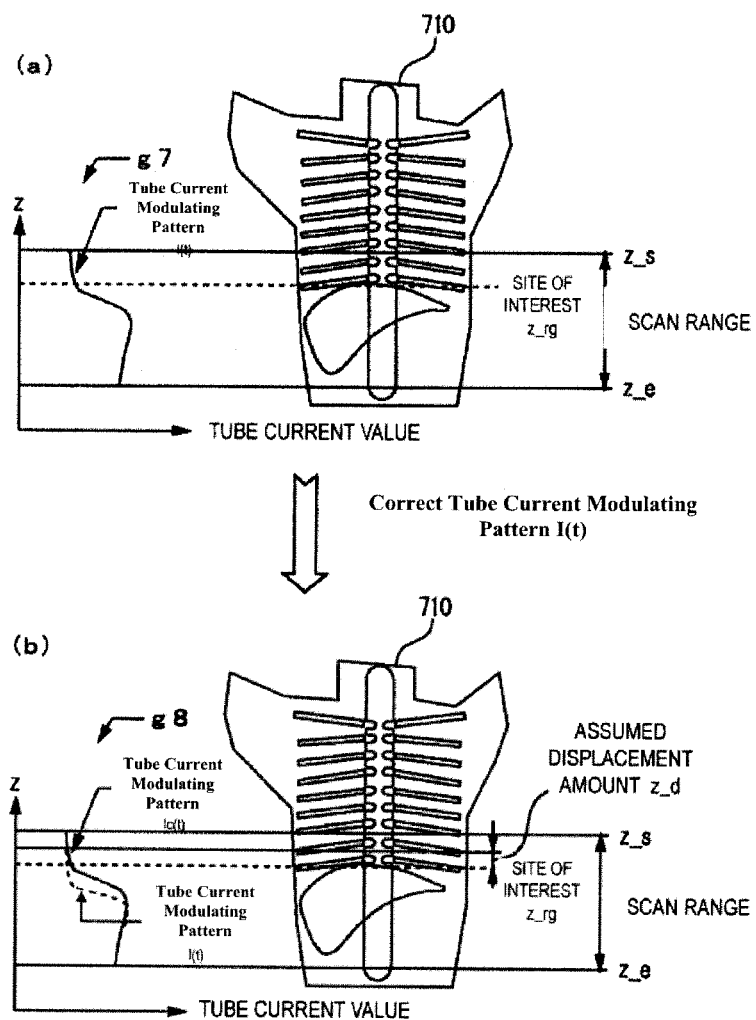
FIG. 14 is a diagram showing correction of the irradiation X-ray dose modulating pattern (tube current modulating pattern).

FIG. 13 is a flowchart showing the flow of the preparation processing when the tube current modulating pattern is directly corrected, and FIG. 14 is a diagram showing the correction of the tube current modulating pattern.

In the flowchart of FIG. 13, the series of processing from the step S201 to the step S210 is the same as the steps from S101 to S110 shown in the flowchart of FIG. 6.

That is, in the preparation processing, the X-ray CT apparatus 1 first executes scanogram imaging, and then makes the operator to input the scan condition (top plate moving pitch, tube voltage set value, scan time, X-ray collimation condition, type of reconstructing filter function, field-of-view size, etc.), the scan range (scan start position, scan finishing position), etc. and also input the desired image quality index value, the z position of the site of interest, the assumed displacement amount. Furthermore, the X-ray CT apparatus 1 generates the three-dimensional cross-section model of the examinee 6 on the basis of the obtained scanogram projection data, and calculates the X-ray attenuation index T(z, β) on the basis of the three-dimensional cross-section model (step S201 to step S210).

With respect to the X-ray attenuation index T(z, β) calculated in step S210, the scan planning unit 405d converts the function of the X-ray attenuation index T from T=T(z, β) to the function T=T(t) of the time [t] on the basis of the scan start position, the scan finishing position, the top plate moving pitch and the scan time (step S211). Subsequently, in the same procedure as described with respect to the step S113 of FIG. 6, the tube current modulating pattern I(t) is calculated by using the mathematical expressions (4) to (9) described above (step S212). Tc in the mathematical expressions (4) to (9) is replaced with T. Thereafter, the scan planning unit 405d corrects the calculated tube current modulating pattern I(t) to a tube current modulating pattern Ic(t) corresponding to the z position and assumed displacement amount of the site of interest (step S213).

In FIG. 14, [z_s] represents the scan start position, [z_e] represents the scan finishing position and the range from the scan start position [z_s] to the scan finishing position [z_e] corresponds to the scan range. In the example of FIG. 14, the position of the site of interest [z_rg] and the position after the assumed displacement of the site of interest are within the scan range.

The curved line shown in a graph g7 of FIG. 14(a) represents a tube current modulating pattern I(t) calculated in step S212. As compared with the scanogram image 710, a curved line on which the tube current value increases in the neighborhood of the site of interest [z_rg] is drawn. In a graph g8 of FIG. 14(b), a curved line indicated by a solid line represents a tube current modulating pattern Ic(t) after correction, and a curved line indicated by a dashed line represents a tube current modulating pattern I(t) before correction.

As shown in FIG. 14(b), the scan planning unit 405d corrects the tube current modulating pattern I(t) to such a curved line that the tube current value increases at a position nearer to the site of interest after the assumed displacement.

The preferred embodiment of the X-ray CT apparatus according to the present invention is described above. However, the present invention is not limited to the above embodiment. For example, in the above embodiment, the gantry type X-ray CT apparatus is described above, however, a C arm type X-ray CT apparatus may be adopted. Furthermore, it is clear that various kinds of modifications or alterations can be made within the scope of the technical idea disclosed in this application by persons skilled in the art, and it is clearly understood that they belong to the technical scope of this invention.

DESCRIPTION OF REFERENCE NUMERALS

1 X-ray CT apparatus, 2 scanner, 3 examinee table, 4 operation table, 5 top plate, 6 examinee, 7 display device, 8 operating device, 201 X-ray tube (X-ray source), 205 X-ray detector, 401 system control device, 405a scanogram image obtaining unit, 405b input unit, 405c cross-section model generator, 405d scan planning unit, 405e X-ray controller, 402 image reconstructing device, 404 storage device, 405 preparation processing executing unit, 405a scanogram image obtaining unit, 405b input unit, 405c cross-section model generator, 405d scan planning unit, 405e X-ray controller, 710 scanogram image, 717 virtual scanogram image.

The invention claimed is:

1. An X-ray CT apparatus for applying X-ray around an examinee, detecting a dose of X-ray transmitted through the examinee, reconstructing a tomogram of the examinee on the basis of the detected X-ray dose and outputting the tomogram characterized by comprising:
   a cross-section model generator that generates a cross-sectional model of the examinee by using scanogram projection data of the examinee;
   an input unit that inputs a desired image quality index value, a position of a site of interest, and an estimated displacement amount of the site of interest in a direction of a body axis during imaging;
   a scan planning unit that sets an irradiation X-ray dose modulating pattern corresponding to the desired image quality index value, the position of the site of interest and the estimated displacement amount input by the input unit by using the cross-section model generated by the cross-section model generating unit and by considering the estimated displacement amount of the site of interest during imaging; and
   an X-ray controller that modulates an irradiating X-ray dose on the basis of the irradiation X-ray dose modulating pattern set by the scan planning unit.

2. The X-ray CT apparatus according to claim 1, further comprising a display unit that displays a scanogram age generated by using the scanogram projection data, wherein the input unit is configured to enable an operator to instruct and input any position on the scanogram image displayed by the display means as a position of the site of interest or a position after an estimated displacement of the site of interest, and the display unit demonstrates on the scanogram image the position of the site of interest or the position after the estimated displacement of the site of interest which is instructed an input by the input unit.

3. The X-ray apparatus according to claim 1, wherein the scan planning unit corrects a scan range in accordance with the estimated displacement amount input by the input unit and sets an irradiation X-ray amount modulating pattern in accordance with the image quality index value, the position of the site of interest and the estimated displacement amount input by the input unit in the corrected scan range with respect to the cross-sectional model generated by the cross-section model generator.

4. The X-ray CT apparatus according to claim 3, further comprising a display unit that displays a scanogram image generated by using the scanogram projection data, wherein the display unit demonstrates a scan range corrected by the scan planning unit on the scanogram image.

5. The X-ray apparatus according to claim 1, wherein the scan planning unit calculates an X-ray attenuation index considering the estimated displacement amount as the irradiation X-ray dose modulating pattern corresponding to the image quality index value, the position of the site of interest and the estimated displacement amount which are input by the input unit, and set an irradiation X-ray dose modulating pattern on the basis of the calculated X-ray attenuation index.

6. The X-ray CT apparatus according to claim 5, further comprising a display unit that displays a scanogram age generated by using the scanogram projection data, wherein at a stage that the X-ray attenuation index considering the estimated displacement amount is calculated by the scan planning unit, the display unit displays a graph corresponding to the X-ray attenuation index so that the graph and the scanogram image are arranged side by side.

7. The X-ray apparatus according to claim 1, wherein the scan planning unit calculates an X-ray attenuation index in advance before estimation of a displacement amount as the irradiation X-ray dose modulating pattern corresponding to the image quality index value, the position of the site of interest and the estimated displacement amount which are input by the input unit, and calculates and sets an irradiation X-ray dose modulating pattern considering the estimated displacement amount on the basis of the calculated X-ray attenuation index.

8. The X-ray CT apparatus according to claim 7, further comprising a display unit that displays a scanogram image generated by using the scanogram projection data, wherein at each stage that the X-ray attenuation index before the displacement amount is estimated is calculated and the irradiation X-ray dose modulating pattern considering the estimated displacement amount is calculated by the scan planning unit, the display unit displays each corresponding graph while the graph and the scanogram image are arranged side by side.

* * * * *